United States Patent [19]

Kearney et al.

[11] Patent Number: 4,805,820
[45] Date of Patent: Feb. 21, 1989

[54] PORTABLE RECEPTACLE

[76] Inventors: Thomas G. Kearney, W221 N2670 Lindenwood Ct.; Charles K. Johnson, 21885 Hillcrest Dr., both of, Waukesha, Wis. 53186

[21] Appl. No.: 171,557

[22] Filed: Mar. 22, 1988

[51] Int. Cl.⁴ .................. B65D 85/14; A45C 11/00
[52] U.S. Cl. .................................. 224/252; 206/37; 206/39; 224/241
[58] Field of Search .............. 224/196, 199, 235, 241, 224/245, 247, 249, 252, 253; 206/37, 37.1, 37.3, 39, 69; 150/149

[56] References Cited

U.S. PATENT DOCUMENTS

| | | | |
|---|---|---|---|
| 1,189,924 | 7/1916 | De Blieux | 224/241 |
| 2,756,913 | 7/1956 | Oswald | 224/196 |
| 4,289,232 | 9/1981 | Seibel | 206/69 |
| 4,741,434 | 5/1988 | Liebman | 206/69 X |

Primary Examiner—Edward L. Roberts
Attorney, Agent, or Firm—Fuller, Puerner & Hohenfeldt

[57] ABSTRACT

A portable receptacle is useful for carrying prophylactic packages. The receptacle is comprised of a generally oval shaped casing closed on one end. Margins of the package are folded over and the package is inserted into the receptacle. The package margins tend to return to their unfolded attitude, thereby exerting force on the casing walls. The package restoring force frictionally resists unintentional removal of the package. One casing wall is formed with a large cutout for facilitating package identification and removal. A cover is pivotable on the casing between the closed position overlying the casing cutout wall and open end, and an open position exposing the package and uncovering the casing open end.

13 Claims, 1 Drawing Sheet

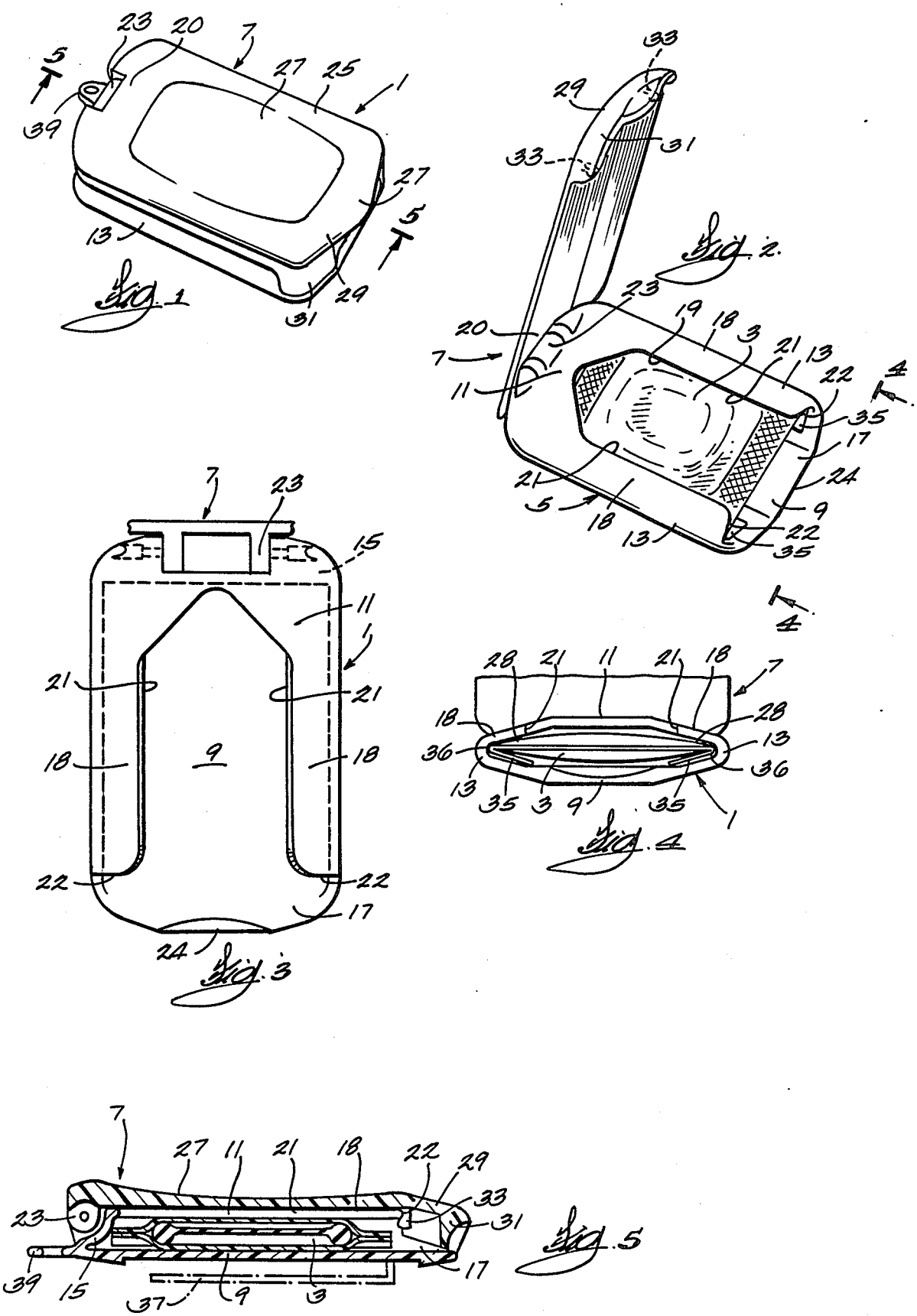

PORTABLE RECEPTACLE

BACKGROUND OF THE INVENTION

1. Field of the Invention This invention pertains to carrying cases, and more particularly to small containers for carrying personal items.

2. Description of the Prior Art The ongoing evolution in social mores has brought into the open certain behavior and products that formerly were more or less discreetly kept out of the public eye. The trend in modern thought, at least among some people, is that conduct once through to be immoral or indecent is actually acceptable.

Whether there is a connection between recent increases in promiscuity and the rise of venereal diseases and Acquired Immune Deficiency Syndrome is open to debate. However, it does seem to safe to state that the spread of venereal disease and AIDS can be inhibited if not prevented by the use of certain types of contraceptives.

Perhaps it is the onslaught of venereal disease and AIDS as much as the relaxation of the moral code that has changed the public attitude toward contraceptives. In former times, the use of contraceptives was a rather secretive affair. Therefore, contraceptive devices such as prophylactics were only quietly advertised, sold and carried. Condoms, for example, often were, and, despite changed perceptions, continue to be, carried hidden in billfolds. However, normal daily activities causes a billfold to chafe the condom packages and to crack or peel them. As a consequence, the package seals are frequently broken, thereby destroying product freshness.

Thus, a need exists for improved means for carrying prophylactics.

SUMMARY OF THE INVENTION

In accordance with the present invention, a portable receptacle is provided that conveniently holds prophylactic packages while protecting them against damage. This is accomplished by apparatus that includes a convertable casing having a pair of grooves for frictionally retaining the packages.

The casing may be generally oval in transverse cross section, with opposed top and bottom walls and opposed curved side walls. One end of the casing is closed; the other end is open. Preferably, the bottom wall extends beyond the edge of the top wall at the casing open end. A rather wide cutout is formed toward the casing closed end. The cutout reduces the top wall to two narrow strips adjacent the side walls for a portion of the length of the top wall. The curved side walls of the casing between the bottom wall and the narrow top wall strips form a pair of opposed grooves. The casing is dimensioned such that the grooves can accept a folded package. The package is folded over along opposed side margins and is inserted into the casing grooves from the open end. The folded margins exert a slight restoring force on the casing walls adjacent the grooves such that the friction aids in retaining the package in the grooves. At the same time, the large cutout and open end in the casing permit easy intentional removal of the package.

The receptacle further comprises a cover that is pivotally connected to the casing closed end. The cover is designed to snap closed over the casing top wall and open end. With the cover closed, the casing bottom wall serves as one exterior wall of the receptacle, and the cover serves as the opposite exterior wall. The cutout casing top wall is enclosed within the receptacle. When the receptacle is being carried, the cover is closed to protect the package. Opening the cover exposes the package for identifying it and removing it from the receptacle.

The receptacle of the present invention may be carried in several ways. It is small enough to be carried in a purse or pocket. The casing bottom wall can be provided with a clip for wearing on a belt. THe receptacle can also be fabricated with a loop for receiving a key chain or necklace for wearing as a pendant. Other advantages and objects of the present invention will become apparent to those skilled in the art upon reading the detailed disclosure.

BRIEF DESCRIPTION OF THE DRAWINGS

FIG. 1 is a perspective view of the portable receptacle of the present invention in the closed position;

FIG. 2 is a perspective view of the portable receptacle of the present invention in the open position;

FIG. 3 is an enlarged fragmentary top view of the present invention in the open position;

FIG. 4 is a view taken along lines 4—4 of FIG. 2; and

FIG. 5 is a cross sectional view taken along lines 5—5 of FIG. 1.

DETAILED DESCRIPTION OF THE INVENTION

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Referring to FIGS. 1-5, a portable receptacle 1 is illustrated that includes the present invention. The receptacle 1 is particularly useful for carrying prophylactic packages 3, but it will be understood that the invention is not limited to use with contraceptive devices.

The receptacle 1 comprises a casing 5 and a cover 7. The casing 5 and cover may be made from any suitable material, but a preferred material is a tough and attractive thermosetting plastic. The casing is preferably generally oval shaped in transverse cross section, as best shown in FIGS. 2 and 4, but other cross sectional shapes are also possible. To that end, the casing has a slightly curved bottom wall 9, a slightly curved top wall 11, and opposed rather sharply curved side walls 13. The casing is closed at one end with a solid wall 15, and it is open at the opposite end 17. The top wall 11 terminates in an edge 22 at the casing open end 17. The bottom wall 9 extends beyond the top wall edge 22 to terminate in an open end edge 24.

A rather large cutout 19 is formed in the top wall 11. The cutout 19 extends from the open end edge 22 toward the closed end 15, thereby creating longitudinally extending top wall strips 18 bounded by longitudinal edges 21. The cutout edges 21 are shown in FIGS. 2 and 3 as terminating in a generally triangular shape near the casing closed end, but other configurations, such as circular or rectangular, are also possible. Looking particularly at FIG. 4, the casing top wall strips 18, side walls 13 and bottom wall 9 cooperate to form opposed longitudinal groves 28.

The cover 7 has a first end 20 that is pivotally attached by a hinge 23 to the casing at the closed end 15 thereof. The cover has a slightly curved lid portion 25 that generally corresponds to the contour of the casing top wall 11. The cover lid portion 25 may include a relatively flat or dished decorative area 27. The cover free end 29 opposite the hinge 23 is formed with a lip 31. When the cover is closed over the casing, the lip 31 overlaps the casing top wall edge 22 and closes the casing open end 17, as is best shown in FIGS. 1 and 5. The cover is further formed with a pair of tabs 22 that depend from the cover lid portion near the free end 29. The tabs 33 are designed to snap over the casing top wall edges 22 for releasably retaining the cover in a closed position over the casing.

The casing grooves 28 are dimensioned and shaped to removably receive one or more packages 3. To aid in holding the packages in place, the package margins 35 are folded over against the main portion of the package along fold lines 36. When inserted into the grooves of the receptacle 1, the fold lines 36 are proximate the casing side walls 13. The folded margins 35 tend to return to their unfolded positions, and in doing so, they exert a force on the casing walls adjacent the side walls 13. The pakcage restoring force produced enough friction between the package and the casing to retain the package within the casing when the cover 7 is in the open position. On the other end, the package is easy to identify and intentionally remove from the casing because of the large cutout 19 and the open end 17. This facilitates manual withdrawl of the package. As mentioned, the casing top wall 11 terminates in edge 22 that lie between the bottom wall edge 24 and the casing closed end 15. The offset between the edges 22 and 24 also contribute to easy removal of the packages from the casing.

The portable receptacle 1 of the present invention may be easy and conveniently carried. It is small and light enough to carry in a pocket or purse. The casing may be furnished with a clip 37 for wearing on a belt. A loop or eye 39 may be molded on the casing 5 for receiving a chain, thereby enabling a person to wear the receptacle on a key chain or as a pendant.

Thus, it is apparent that there has been provided, in accordance with the invention, a portable receptacle that fully satisfies the aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A portable receptacle comprising:
  a. a casing having opposed top and bottom walls and opposed side walls and a closed end to form an open end container, the bottom wall terminating at the casing open end at an edge located farther from the casing closed end than the top wall open end edge, the casing top, bottom, and sides cooperating to define a pair of opposed grooves sized to removably receive a predetermined package through the open end; and
  b. a cover pivotally attached to the casing at the closed end thereof and adapted to selectively overlie the casing top wall when in a closed position and to expose the casing top wall when in an open position, the cover having a lip adapted to close the casing open end when the cover is in the closed position.

2. The portable receptacle of claim 1 wherein the casing top wall defines a cutout extending from the casing open end edge thereof toward the casing closed end to thereby partially expose a package retained in the casing grooves.

3. The portable receptacle of claim 1 wherein the cover comprises tab means for releasably engaging the top wall end edges at the casing open end when the cover is in the closed position to thereby releasably retain the cover in the closed position.

4. The portable receptacle of claim 1 further comprising clip means attached to the casing for enabling a person to wear the receptacle on a belt.

5. The portable receptacle of claim 1 further comprising loop means joined to the casing for enabling a person to wear the receptacle on a chain.

6. The portable receptacle of claim 1 wherein the casing top, bottom and side walls cooperate to define a generally oval shaped cross section.

7. The portable receptacle of claim 1 wherein the grooves are sized to receive folded margins of the product and wherein the package restoring force retains the product in the grooves.

8. A receptacle for carrying a predetermining package having margins folded against the package along fold lines comprising:
  a. a casing having opposed top and bottom walls with first and second ends and opposed side walls, the top, bottom, and side walls being arranged into a generally ovular shaped container having a closed and an open end, the top wall being formed with a cutout extending from the casing open end toward the closed end, the top, bottom, and side walls being dimensioned to removably receive the folded package into the casing open end with the package fold lines adjacent the casing side walls; and
  b. a cover comprising:
    i. a lid portion pivotally attached to the casing closed end for selectively pivoting between a closed position overlying the casing top wall and an open position wherein the top wall and the package in the casing are exposed; and
    ii. lip means depending from the lid portion for closing the case open end when the lid portion is in the closed position.

9. The receptacle of claim 8 wherein the casing top wall terminates between the casing bottom wall end edges and the casing closed end.

10. The receptacle of claim 9 wherein the cover further comprises tab means depending from the lid portion for releasably engaging the casing top wall to releasably retain the cover in the closed position.

11. The receptacle of claim 10 further comprising clip means joined to the casing for permitting wearing the receptacle on a belt.

12. The receptacle of claim 10 further comprising loop means for receiving a chain to thereby permit carrying the receptacle on a key chain or necklace.

13. The receptacle of claim 8 wherein:
  a. the casing side, top, and bottom walls define opposed grooves for receiving the folded over margins of the package in the grooves; and
  b. the casing walls resist a restoring force exerted by the package margins to thereby frictionally restrain removal of the package from the casing,
so that the package does not fall from the casing when the cover is in the open position.

* * * * *